US011642442B2

(12) United States Patent
Felber et al.

(10) Patent No.: US 11,642,442 B2
(45) Date of Patent: May 9, 2023

(54) BABY BOTTLE WITH MILK PUMP

(71) Applicant: MEDELA HOLDING AG, Baar (CH)

(72) Inventors: Armin Felber, Lucerne (CH); Martin Thüring, Sins (CH); Sebastian Höner, Thalwil (CH)

(73) Assignee: MEDELA HOLDING AG, Baar (CH)

(*) Notice: Subject to any disclaimer, the term of this patent is extended or adjusted under 35 U.S.C. 154(b) by 363 days.

(21) Appl. No.: 17/055,049

(22) PCT Filed: May 24, 2019

(86) PCT No.: PCT/EP2019/063500
§ 371 (c)(1),
(2) Date: Nov. 12, 2020

(87) PCT Pub. No.: WO2019/224365
PCT Pub. Date: Nov. 28, 2019

(65) Prior Publication Data
US 2021/0205510 A1    Jul. 8, 2021

(30) Foreign Application Priority Data

May 25, 2018 (EP) ..................... 18174358

(51) Int. Cl.
*A61M 1/06* (2006.01)
*A61J 9/00* (2006.01)
(Continued)

(52) U.S. Cl.
CPC ............... *A61M 1/062* (2014.02); *A61J 9/00* (2013.01); *G01F 23/00* (2013.01); *G01F 23/14* (2013.01);
(Continued)

(58) Field of Classification Search
CPC ......... A61M 1/062; A61M 9/00; G01F 23/00; G01F 23/14; G01F 23/20
(Continued)

(56) References Cited

U.S. PATENT DOCUMENTS 2,773,385 A * 12/1956 Johnson ............... G01C 13/004
73/170.31
4,535,627 A * 8/1985 Prost ....................... G01G 23/28
367/908
(Continued)

FOREIGN PATENT DOCUMENTS

| CN | 105267044 A | 1/2016 |
| CN | 105943399 A | 9/2016 |

(Continued)

OTHER PUBLICATIONS

Australian Examination Report No. 1 for Application No. 2019273688, dated May 21, 2021.
(Continued)

*Primary Examiner* — John Fitzgerald
(74) *Attorney, Agent, or Firm* — Marshall, Gerstein & Borun LLP

(57) ABSTRACT

The present invention relates to an apparatus (2) comprising a connector (4), a baby bottle (6) which can be coupled thereto having a bottle body (8) and a bottle base (10), and a sensor unit (34) arranged in the bottle base (10) for determining the filling quantity of milk in the baby bottle (6). An object of the present invention is to improve handling and maintenance of the apparatus, as well as determining the content quantity. It is characterized in that the bottle base (10) is releasably attachable to the bottle body (8).

10 Claims, 10 Drawing Sheets

(51) Int. Cl.
*G01F 23/00* (2022.01)
*G01F 23/14* (2006.01)
*G01F 23/20* (2006.01)

(52) U.S. Cl.
CPC .......... *G01F 23/20* (2013.01); *A61J 2200/76* (2013.01); *A61M 2205/0216* (2013.01); *A61M 2205/0233* (2013.01); *A61M 2205/3389* (2013.01)

(58) Field of Classification Search
USPC .......................... 73/149, 295, 299, 300, 301
See application file for complete search history.

(56) References Cited

U.S. PATENT DOCUMENTS

| | | | | |
|---|---|---|---|---|
| 6,079,266 | A * | 6/2000 | Wright | ................ G01F 23/2966 73/299 |
| 7,506,541 | B2 * | 3/2009 | Woodard | ................ G01F 22/00 73/304 R |
| 2005/0056611 | A1 * | 3/2005 | Hakim | ..................... A61J 11/00 215/396 |
| 2010/0012395 | A1 | 1/2010 | Mannhart et al. | |
| 2012/0017689 | A1 * | 1/2012 | Giordano | ............ A47L 15/4244 73/722 |
| 2015/0283311 | A1 | 10/2015 | Alvarez et al. | |
| 2016/0377497 | A1 * | 12/2016 | Nackaerts | ........... B81C 1/00246 73/862.626 |
| 2017/0021068 | A1 | 1/2017 | Gaskin et al. | |

FOREIGN PATENT DOCUMENTS

| | | |
|---|---|---|
| CN | 106137768 A | 11/2016 |
| CN | 206730161 U | 12/2017 |
| JP | S60-177843 U | 11/1985 |
| JP | 2010-507784 A | 3/2010 |
| JP | 2017-509379 A | 4/2017 |
| KR | 20120123234 A * | 11/2012 |
| WO | WO-2015/173042 A1 | 11/2015 |
| WO | WO-2016014469 A1 | 1/2016 |
| WO | WO-2016164853 A1 * | 10/2016 ............... A61J 9/00 |
| WO | WO-2017/186504 A1 | 11/2017 |
| WO | WO-2018/045349 A1 | 3/2018 |

OTHER PUBLICATIONS

Australian Examination Report No. 2 for Application No. 2019273688, dated Aug. 31, 2021.
Australian Examination Report No. 3 for Application No. 2019273688, dated Jan. 11, 2022.
Australian Examination Report No. 4 for Application No. 2019273688, dated Apr. 27, 2022.
Australian Notice of Acceptance for Application No. 2019273688, dated May 24, 2022.
Translation of Notice of Reasons for Rejection for Japanese Patent Application No. 2020-565834, dated Dec. 14, 2021.
Taiwan Office Action for Application 11020678780, dated Jul. 15, 2021.
Taiwan Office Action for Application No. 108118030, dated May 6, 2022.
European Search Report for Application No. 18174358, dated Nov. 9, 2018.
International Search Report with Translation for Application No. PCT/EP2019/063500, dated Aug. 1, 2019.

* cited by examiner

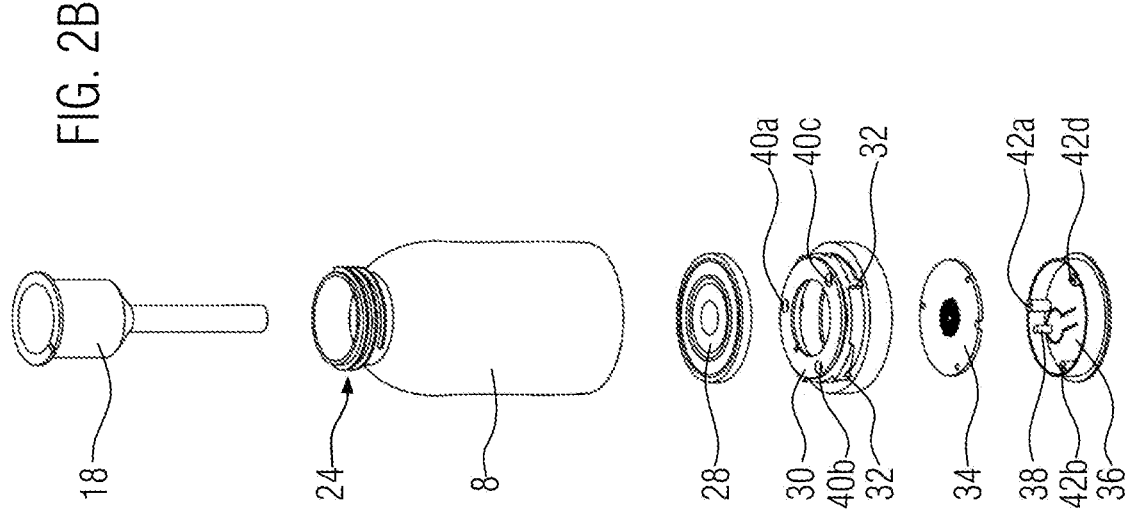
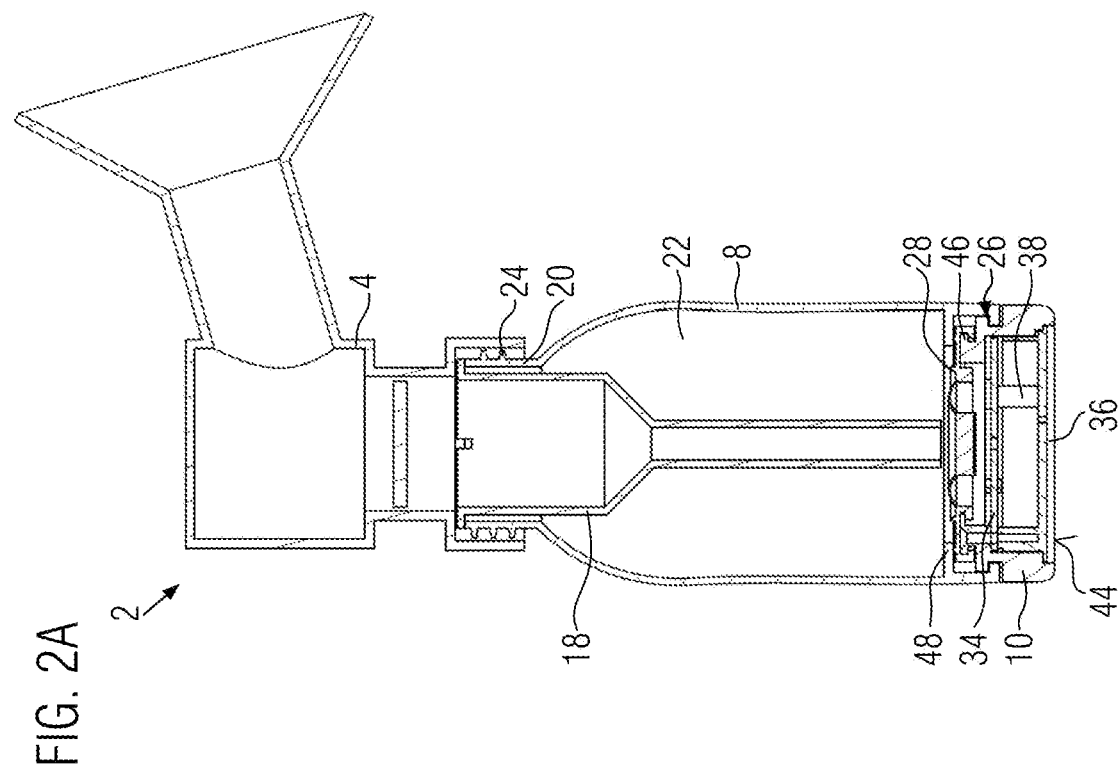

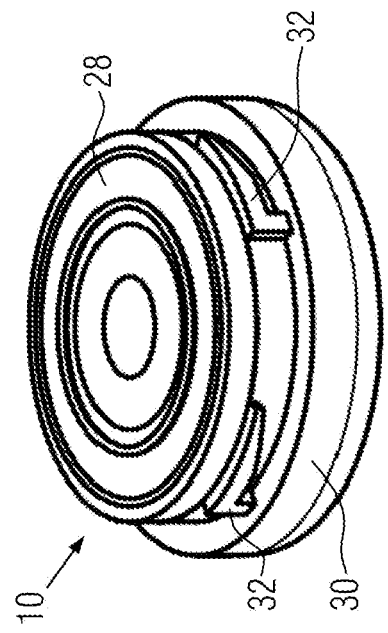
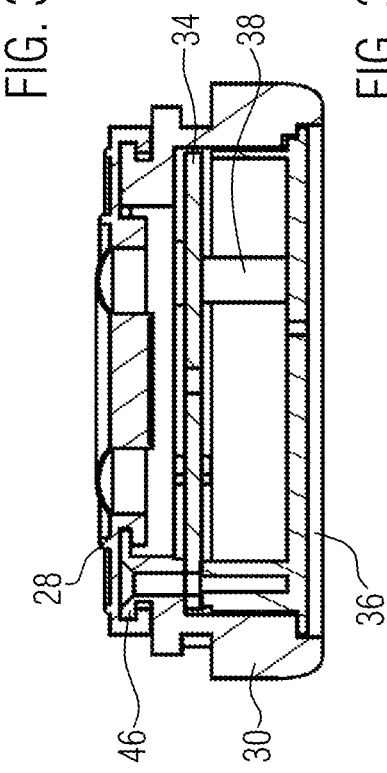
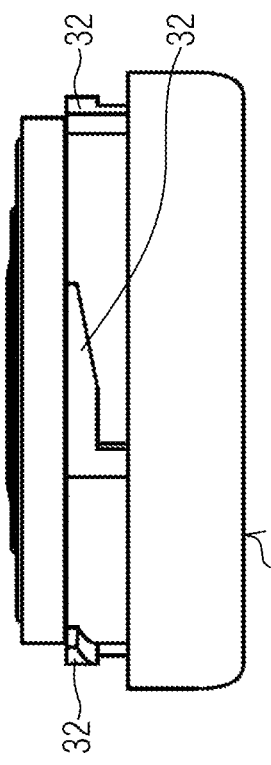
FIG. 3B
FIG. 3C
FIG. 3D
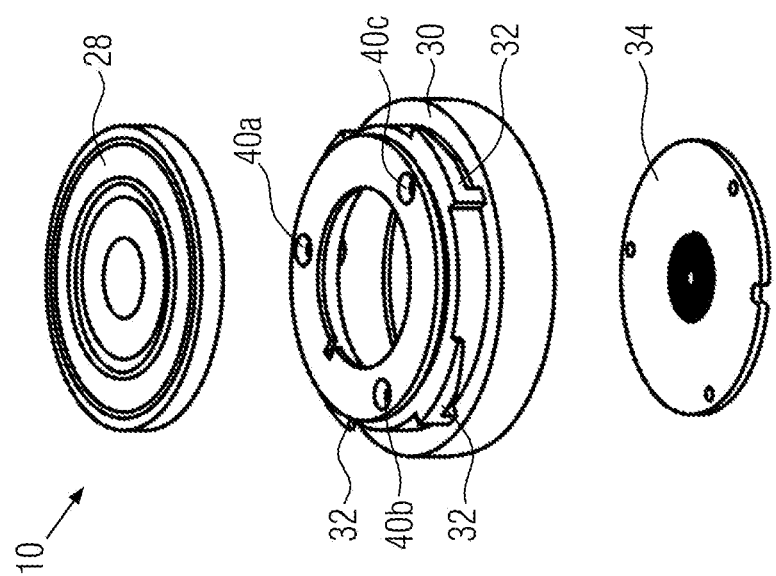
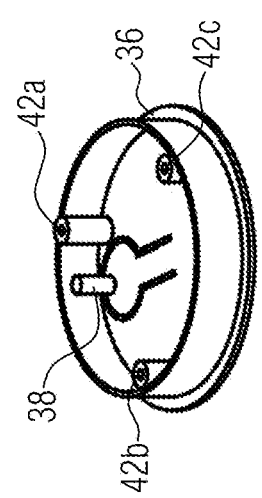
FIG. 3A

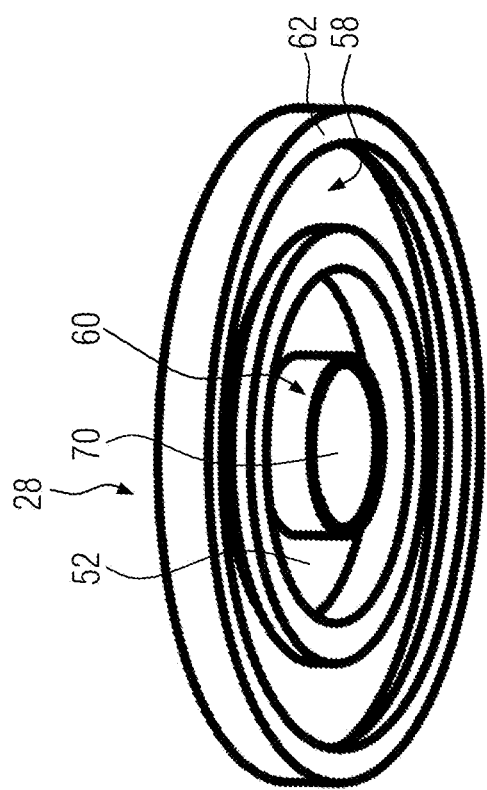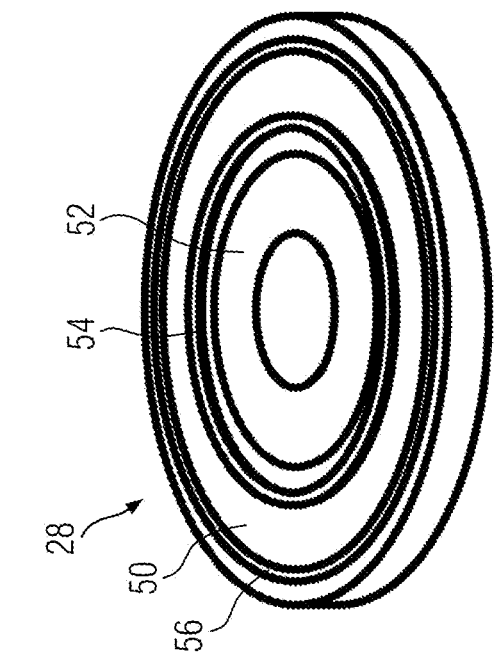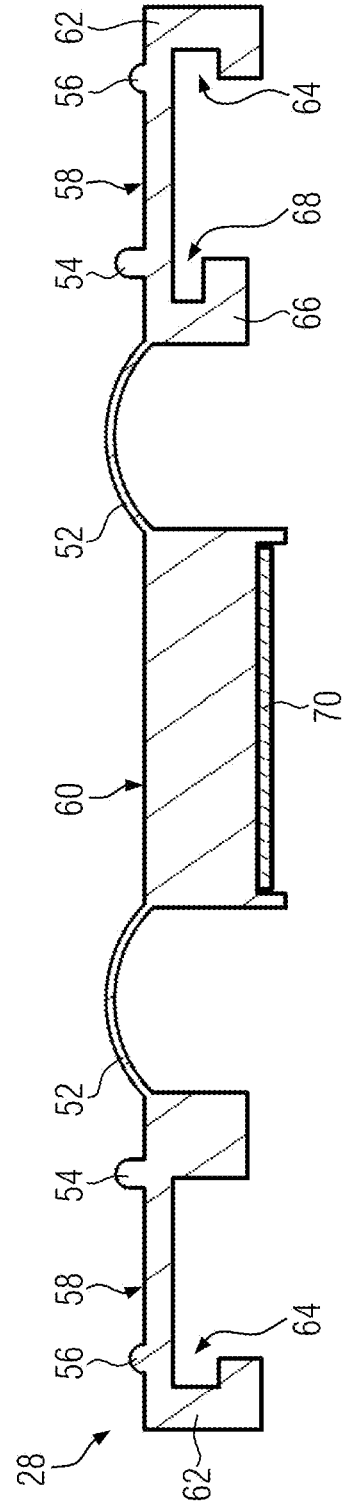

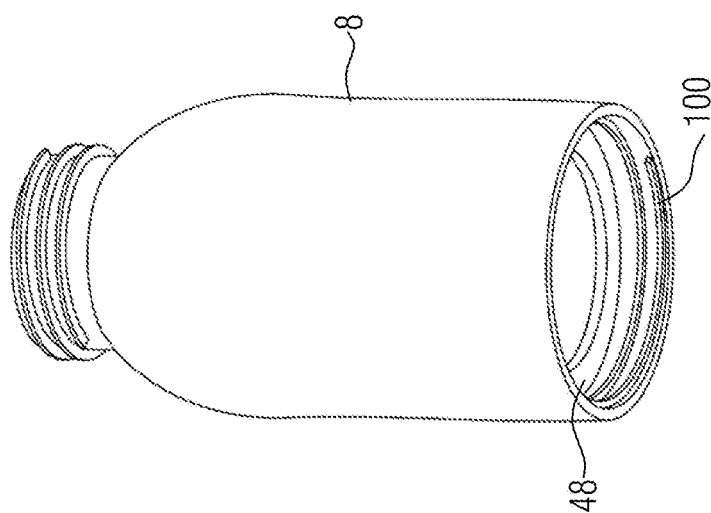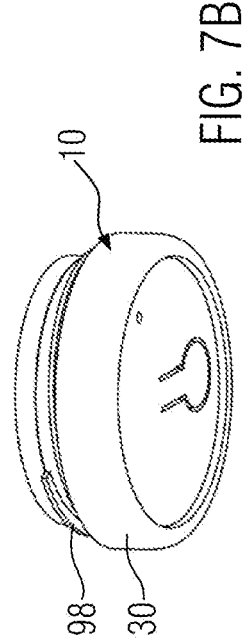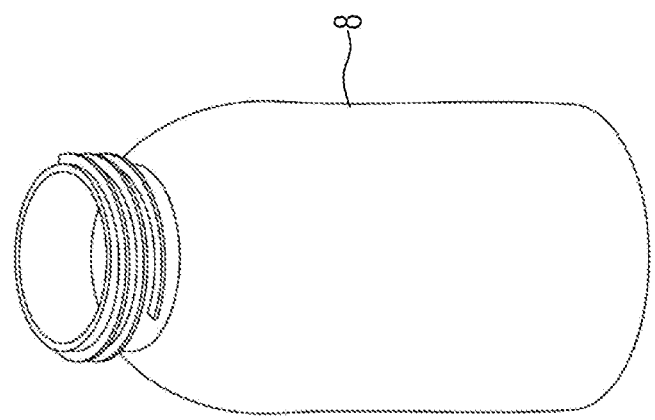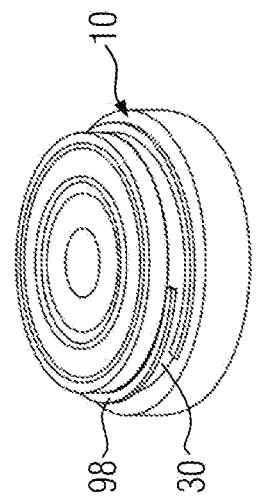
FIG. 7A
FIG. 7B

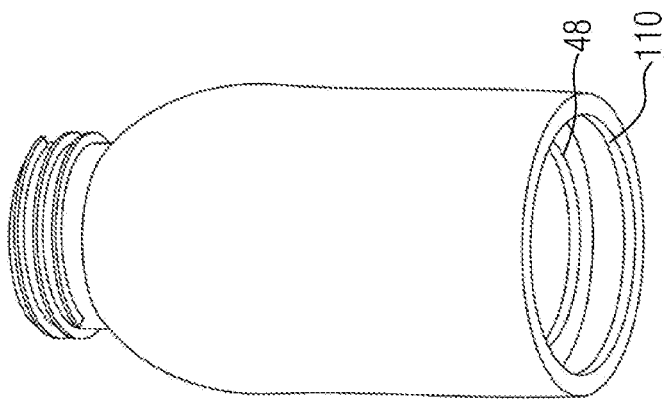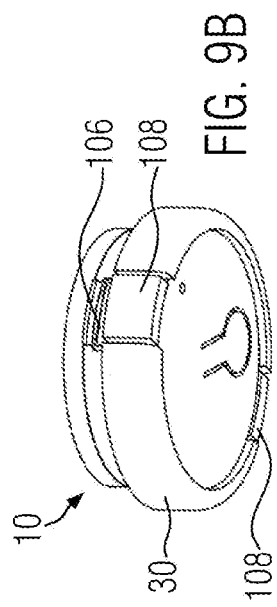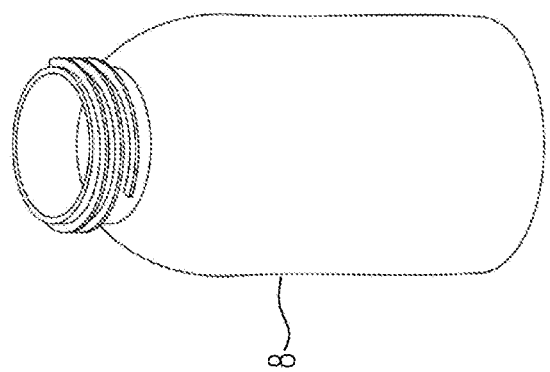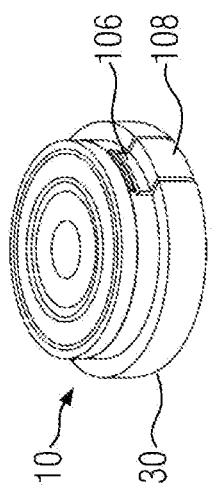

BABY BOTTLE WITH MILK PUMP

CROSS-REFERENCE TO RELATED APPLICATION

This present application is the US national phase of International Patent Application No. PCT/EP2019/063500, filed May 24, 2019, which claims priority to European Application No. 18174358.4, filed May 25, 2018. The priority application, EP 18174358.4, is hereby incorporated by reference in its entirety.

FIELD OF THE DISCLOSURE

The present invention relates to an apparatus comprising a connector, a baby bottle which can be coupled thereto having a bottle body and a bottle base, and a sensor unit arranged in the bottle base for determining the filling quantity of milk in the baby bottle. This apparatus can also be referred to as a pump unit.

BACKGROUND

US 2015/0283311 A1 describes an apparatus comprising a baby bottle with a reservoir that is on its neck screwed to a connector. When the baby bottle stands upright, a plate forms the lower boundary of the reservoir and the weight of fluid collected in the reservoir rests on the plate. A strain gauge is arranged on the oppositely disposed side of the plate and registers the increase or decrease of the weight load on the plate. Based on this measurement, the filling quantity of the baby bottle can be calculated.

The prior art apparatus has room for improvement.

SUMMARY OF THE DISCLOSURE

An object of the present invention is to improve handling and maintenance of the apparatus, as well as determining the content quantity.

To satisfy this object, the present invention proposes an apparatus characterized in that the bottle base is releasably attachable to the bottle body.

The bottle base with the sensor unit arranged therein can then be separated from the bottle body. This makes the sensor unit easier to access for maintenance or repair purposes, and the bottle body can be cleaned better. Furthermore, the design of the bottle body is not impaired by the sensor unit.

The baby bottle according to the invention is typically produced from at least partially transparent thermoplastic material or from glass. Particularly preferably, polypropylene is used. The baby bottle made of plastic material can be produced as a disposable bottle or as a returnable bottle and usually has a weight of 7.5 to 30 g. The reusable baby bottle preferably has a wall thickness of about 0.9 mm.

The nominal volume of the baby bottle is typically 80 to 250 ml, in particular 80 ml, 150 ml or 250 ml. The maximum volume that the baby bottle can accommodate is usually no greater than 330 ml.

The baby bottle preferably has a height of about 60 to 160 mm, preferably 66 mm, 99.5 mm, 102 mm, 136 mm or 148.5 mm. The diameter of the bottle neck forming an opening is typically 33 mm. The maximum diameter of the bottle is typically no greater than 50 to 70 mm, preferably no greater than 53 mm, 60 mm or 65 mm. All dimensions are to be understood having a tolerance of ±10%, preferably ±5%.

In general, the bottle has a substantially cylindrical bottle body, which tapers conically toward a bottleneck, wherein the bottleneck can be connected to a breast pump and/or a teat. The diameter of the body of the bottle can also vary over its length. For example, the bottle body can have several cylindrical sections of different diameters which can, in particular, be connected by one or more conically shaped sections. The bottleneck usually has the smallest diameter. The bottleneck is preferably provided with an external thread.

The bottle base usually forms a bearing surface on which the baby bottle stands upright on a flat support surface. That part of the baby bottle is generally referred to as the bottle base which extends from the bearing surface to a separating element impermeable to fluid which defines a fluid reservoir of the baby bottle in the direction of the bearing surface. The separating element can be associated with the bottle body or the bottle base. The removable bottle base is generally disc-shaped with a height of about 1 to 3 cm. The diameter of the removable bottle body usually corresponds to that of the base end of the bottle body, but can differ up to 20 mm therefrom. The bearing surface is typically a substantially planar surface which can optionally have a central curvature inwardly towards the reservoir. The bearing surface can also be formed by a downwardly projecting ring.

A connector typically comprises a breast shield that is adapted to the female human breast, and can in particular be sealingly applied thereto, and that is connectable to and adapted to interact with a hand pump or an electrically operated pump to generate negative pressure between the breast shield and the breast. The negative pressure is typically generated at a certain frequency corresponding to the pumping or suction strokes of the pump. This stimulates the milk flow. The connector usually has a channel that drains milk collected in the breast shield into the baby bottle, provided the connector is connected to the baby bottle. A flap valve is typically provided in the channel and remains closed during the pumping or suction stroke. During the opposite stroke, the flap valve opens and milk flows through. The apparatus preferably includes a funnel formed adapted to introduce milk centrally into the lower end of the reservoir, i.e. the end at the side of the bearing surface.

According to one preferred further development of the present invention, the sensor unit comprises an inductive sensor, preferably an eddy current sensor. Inductive sensor units are part of the class of non-contact measuring equipment. They are robust and insensitive to fouling and interference fields. In addition, they are inexpensive.

The apparatus preferably comprises a separating element impermeable to fluid that is movable in the direction of the sensor unit and that comprises a measuring element made of electrically highly conductive material. The separating element can be made of elastic material and possibly be fixed to the baby bottle at the edge and exhibit movability within the meaning of elastic deformation. The separating element can just as well be formed as a rigid component and be slidably disposed in the baby bottle. In the case of a rigid separating element, it is preferable to support it by at least one pre-tensioning element in the bottle base. In both cases, the separating element is preferably configured such that, without the force effect of the weight force of a filling quantity of milk, i.e. when the baby bottle is empty, it returns to its original position or remains there, respectively. Preferably, the separating element is configured as a separate component which can be easily removed and cleaned or sterilized by releasing the bottle base from the bottle body. The separating element can, in particular, be positioned in the baby bottle such that it closes the reservoir in the direction of the bottle base in a fluid-tight manner and separates the bottle base from the bottle body in a fluid-tight manner. The measuring element is typically arranged on the side of the separating element disposed opposite the reservoir. Both the sensor unit as well as the measuring element are then separated from the milk in the baby bottle, so that failure-free measurement can be ensured.

According to a further preferred development of the present invention, the separating element impermeable to fluid is configured such that—when the baby bottle stands upright—it moves toward the sensor unit when the filling quantity of milk increases and away from the sensor unit when the filling quantity of milk decreases. The distance of the measuring element from the sensor unit decreases with increasing filling quantity of milk in the baby bottle. Sensitive measurement of this distance enables particularly accurate determination of the filling quantity of milk in the baby bottle.

The separating element impermeable to fluid is preferably formed as an elastic membrane with a centrally arranged metallic insert or a metallic coating. More preferably, the sensor unit comprises a coil which is arranged centrally in the bottle base and spaced from the membrane.

The metallic insert or the metallic coating then form the measuring element. The magnetic field of the coil is there influenced by eddy currents induced in the measuring element, where this influence is proportional to the distance between the metallic insert or the metallic coating, respectively, and the coil. The degree of influence and its temporal change on the magnetic field of the coil can be detected, for example, by way of an RLC oscillator circuit which can likewise be arranged in the bottle base. Even when the baby bottle is filled to the maximum, a minimum distance or gap between the measuring element and the coil of approximately 1 mm preferably remains.

The RLC oscillator circuit is preferably provided on a circuit board (PCB). This proves to be a space-saving and cost-effective solution for detecting the magnetic field changes of the coil.

According to one preferred embodiment of the present invention, the axis of the metallic insert is at least approximately aligned with the axis of the coil. Particularly preferably, the axis of the metallic insert is arranged coaxially with the axis of the coil. This increases the measuring accuracy. The axis of the metallic insert is to be understood, in particular, as being the longitudinal axis or, in the case of a radially symmetrical insert, the axis of symmetry. Suitable as a metallic insert is, for example, a preferably disc-shaped copper plate or a plate made of stainless steel or anodized aluminum.

According to one further preferred development of the present invention, electronic components are arranged between the coil and the bearing surface formed by the bottle base. In particular, the electronic components together with the coil form the RLC oscillator circuit. However, other electronic components, such as a microprocessor or a position sensor, can be provided. Particularly preferably, the electronic components are provided on a circuit board (PCB) on which also the coil is arranged. The circuit board and the coil preferably comprise a central hole. Air pressure, which is caused by the motion of the separating element in the direction of the sensor, can be compensated therewith.

The bottle base is attachable to the baby bottle preferably by screwing, a bayonet lock or a snap lock. In the case of a bayonet lock, the bottle base preferably comprises at least one locking arm having an undercut and the bottle body comprises at least one locking bead on its inner circumference parallel to the undercut. In the case of screwing, it is preferable for a compact configuration that an internal thread is provided on the inner circumferential surface of the bottle body and a mating thread on the bottle base. But the bottle base can just as well form an internal thread and the bottle body an external thread as a mating thread. In the case of a snap lock, the bottle base preferably comprises at least one locking catch which can be resiliently retained by manual actuation, in order to lock it behind a catch projection formed on the bottle body when the bottle base and the bottle body are joined. The catch projection is preferably formed as a circumferentially continuous bead on the inner circumferential surface of the end of the bottle body facing the bottle base.

On the inner circumferential surface of the end section of the bottle body facing the bottle base, the bottle body preferably comprises a ring-shaped flange against which the bottle base or the separating element abuts in a sealing manner. More preferably, the separating element is forced or fixed against the flange when the bottle body is joined with the bottle base.

In an independent aspect, the present invention provides a baby bottle with a bottle body, a bottle base and a sensor unit arranged in the bottle base for determining the quantity of content in the bottle, wherein the bottle base is releasably attachable to the bottle body. The bottle is preferably configured as defined above, and particularly preferably further developed according to one or more of the developments discussed above.

BRIEF DESCRIPTION OF THE SEVERAL VIEWS OF THE DRAWING

Further details of the present invention shall become apparent from the following description of an embodiment of the invention in combination with the drawing, in which:

FIG. 2A shows a longitudinal sectional view of a second embodiment,

FIG. 2B shows an exploded view of the second embodiment of FIG. 2A (without the connector), FIG. 3A shows an exploded view of the bottle base of the first and second embodiments, FIG. 3B shows a perspective view of an assembled bottle base, FIG. 3C shows a longitudinal section view of the assembled bottle base of FIG. 3B, FIG. 3D shows a side view of the assembled bottle base of FIG. 3B, FIG. 4A shows an enlarged top perspective view of a membrane of the first and second embodiments, FIG. 4B shows an enlarged bottom perspective view of the membrane of FIG. 4A, FIG. 4C shows a longitudinal section view of the membrane of FIG. 4A, FIG. 7A shows a partially exploded top perspective view of a third embodiment, FIG. 7B shows a partially exploded bottom perspective view of the third embodiment, FIG. 9A shows a partially exploded top perspective view of a fifth embodiment, FIG. 9B shows a partially exploded bottom perspective view of the fifth embodiment.

DETAILED DESCRIPTION OF THE PREFERRED EMBODIMENTS

Figure 1A:
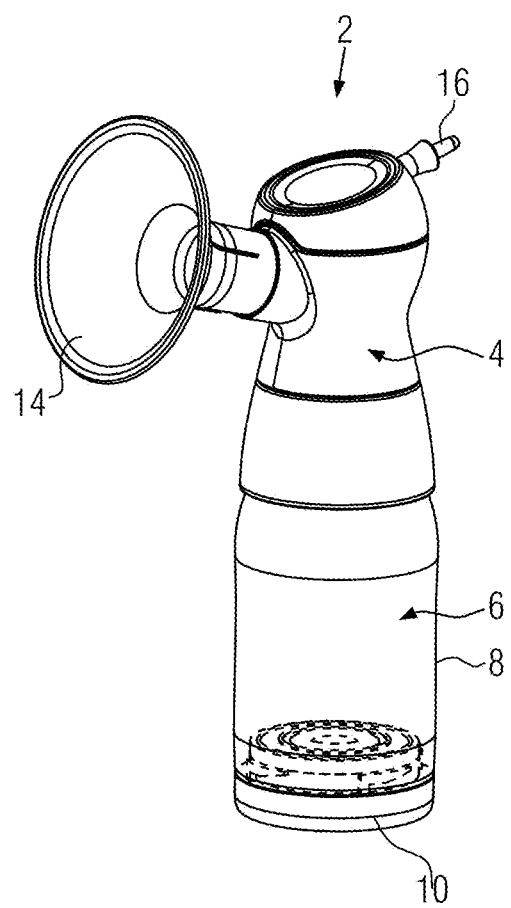
FIG. 1A shows a side view of an embodiment.
Figure 1B:
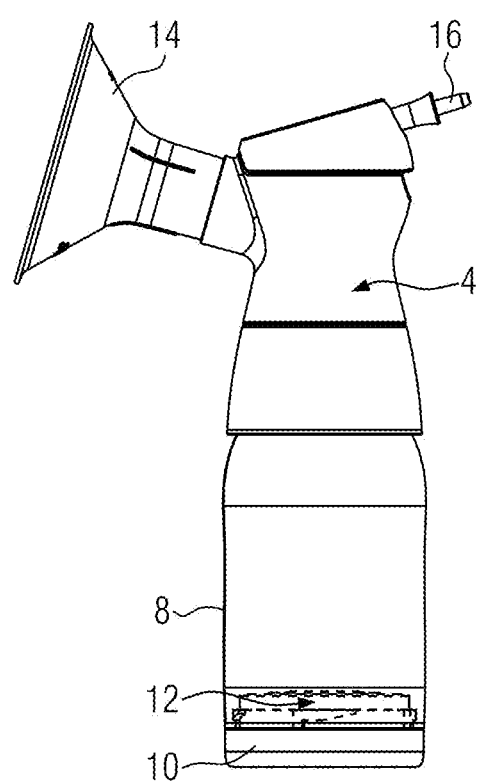
FIG. 1B shows a side view of the embodiment of FIG. 1A filled with milk.

FIG. 1A shows an embodiment of the apparatus 2 according to the invention. The apparatus 2 is a pump unit and comprises a connector 4 which is attached to a baby bottle 6 by way of a screw connection (not shown). The baby bottle 6 has a substantially cylindrical bottle body 8 and a bottle base 10. The bottle 8 in the present embodiment is produced from transparent polypropylene. A separating element 12 impermeable to fluid arranged in the baby bottle 6 can therefore be seen. The separating element 12 impermeable to fluid seals a reservoir of the bottle body 8 in a fluid-tight manner against the bottle base 10. This is illustrated in FIG. 1B, in which the baby bottle filled with milk is shown. In FIGS. 1A and 1B, the bottle base 10 is connected to the bottle body 8. This connection is releasable.

The connector 4 comprises a breast shield 14 which can be applied against a female breast in a sealing manner, and a connection 16 for a breast pump.

Same components in the embodiments described below are provided with the same reference numerals.

FIG. 2A shows a sectional view of a second embodiment of the apparatus 2 according to the invention. As compared to the embodiment of FIG. 1, the apparatus additionally comprises a funnel 18 which is inserted into the bottle neck 20 of the bottle body 8 and extends until just before the base-side end of the fluid reservoir 22 of the baby bottle 8. The funnel 18 is arranged centered in the baby bottle.

FIG. 2B shows an exploded view of the embodiment of FIG. 2A, where the connector, which can be a conventional one, is omitted. The bottle body 8 has an external thread 24 on the bottle neck 20 via which the connector 4 is screwed to the bottle body 8. The bottle base 10 is attached to the bottle body 8 by way of a bayonet lock 26. A substantially disc-shaped elastic membrane 28 is provided as a separating element 12 impermeable to fluid and is supported by a housing 30 which forms locking arms 32 for the bayonet lock 26 (see also FIG. 3D). Disposed in the bottle base 10 is a sensor unit 34 which is shown in FIG. 2B as a populated disk-shaped circuit board. The bottle base 10 further comprises a housing cover 36 with a distance-bridging pin 38 that actuates an on/off switch which shall be explained in more detail below. The housing cover 36 is fixedly connected, preferably screwed to the housing 30 by way of mounting holes 40a, 40b, 40c in the housing 30, on the one hand, and 42a, 42b, 42c in the housing cover 36, on the other hand, which are associated with one another. The housing cover 36 forms a flat bearing surface 44, on which the baby bottle 6 stands upright, provided the baby bottle 6 is placed on a flat support surface. In the embodiment, the baby bottle is supported on a flat bearing surface which is formed by a lower ring recognizable in FIG. 2A.

The outer edge of the membrane 28 is slipped over a housing flange 46, so that the elastic membrane 28 is connected to the housing 30 in a positive-fit manner (see also FIG. 3C). Due to its elasticity, however, the membrane 28 can again be removed, in particular manually, from the housing flange 44 after the bottle base 10 has been released from the bottle body 8. The upper side of the outer edge of the membrane 28 is forced by the housing 30 against a ring-shaped flange 48 formed at the lower end section of the bottle body 8 at the inner circumference thereof.

FIGS. 3A to 3D show various enlarged views of the bottle base 10 of the first and the second embodiment. FIG. 3A is an exploded view and depicts the elastic membrane 28, the housing 30, the sensor unit 34 and the housing cover 36. FIG. 3B shows a perspective side view of the bottle base 10 assembled from the components shown in FIG. 3A.

In FIGS. 4A, 4B and 4C, the substantially disk-shaped elastic membrane 28 of the first and the second embodiment is shown enlarged, where FIG. 4A shows the upper side, FIG. 4B the underside and FIG. 4C a longitudinal sectional view of the membrane. Formed on the substantially planar upper side 50 of the membrane 28 are three different rings projecting from the planar surface 50: an inner arcuate ring 52, a center ring 54 and an outer ring 56. In the region of the arcuate inner ring 52, the membrane 28 has the smallest thickness. The arcuate inner ring 52 connects an outer attachment section 58 to an inner movable section 60. While the outer attachment segment 58 abuts against the housing 30 and can be slipped, via a flange 62 with undercut 64 circumferential closed at the edge, over the housing 30 and connected in a positive-fit manner, the arcuate inner ring 52 and the movable section 60 are held freely in the housing 30 i.e. are not supported by the housing 30.

In the present case, the outer attachment section 58 comprises at least one second flange 66 with an undercut 68 at the radially inner end of the attachment section 58. The arcuate inner ring 52 is elastically deformable and therefore enables the movability of the movable section 60 orthogonally to the planar upper side 50 of the membrane 28. On its underside, the movable inner section 60 comprises a copper plate 70 as the metallic insert.

Figure 5B:
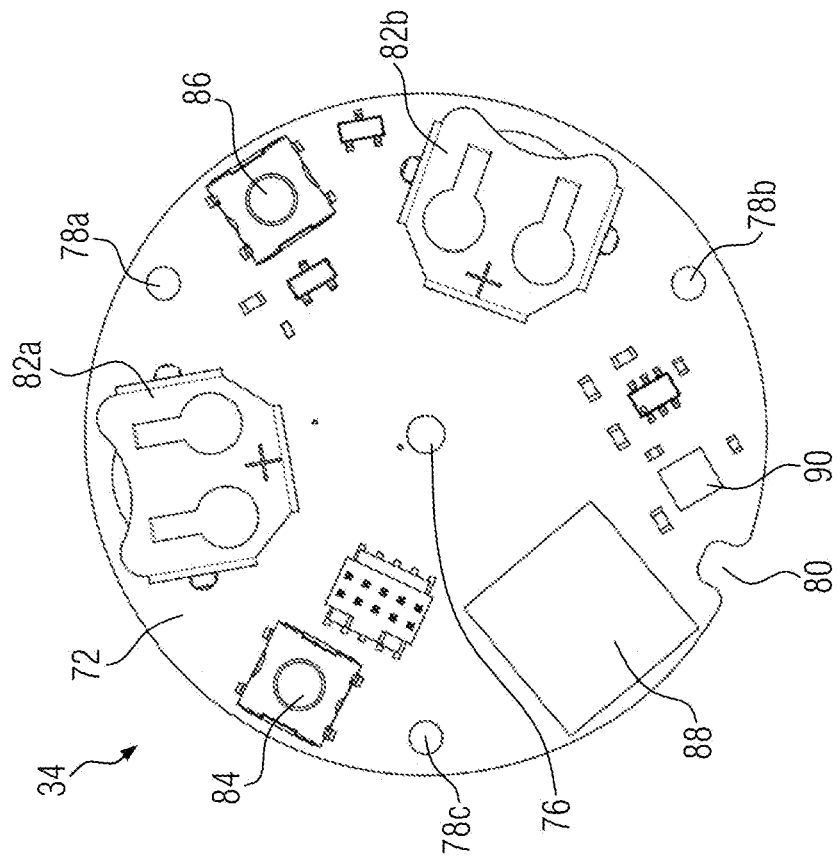
FIG. 5B shows a bottom view of the circuit board of FIG. 5A.
Figure 5A:
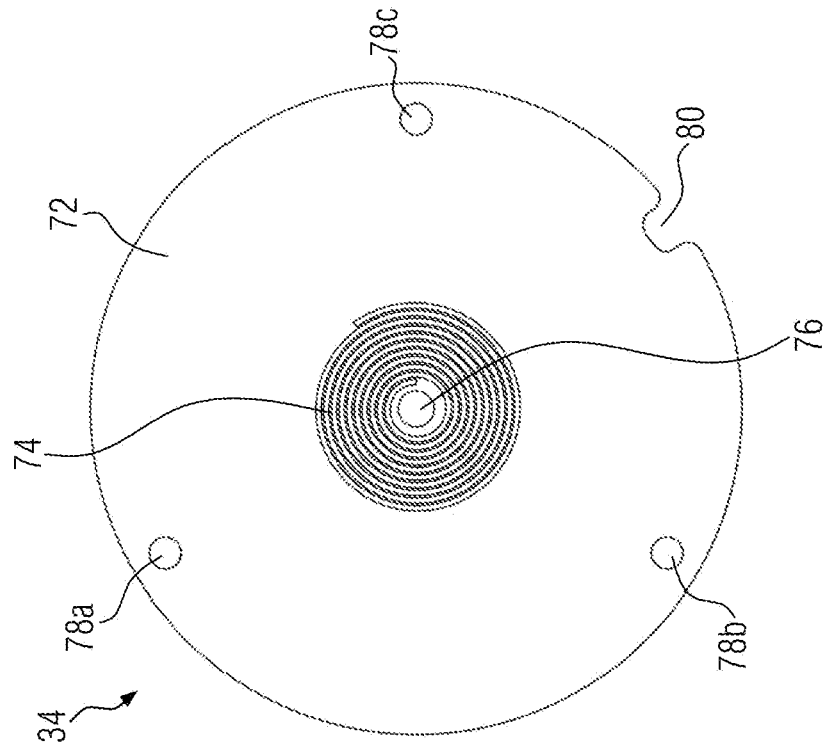
FIG. 5A shows a top view of a circuit board of the first and second embodiment with a sensor unit.
Figure 6B:
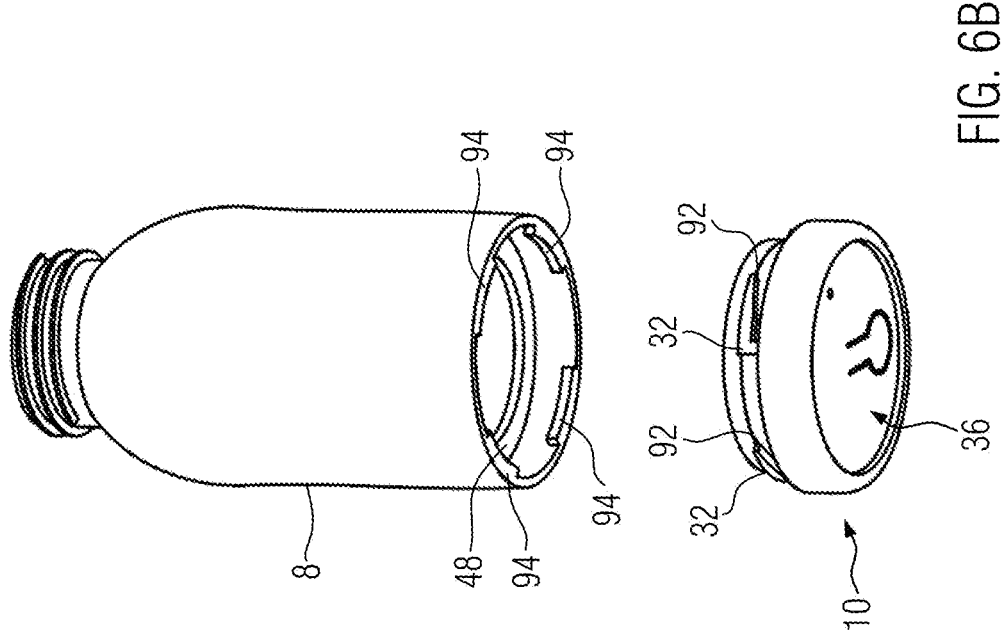
FIG. 6B shows a partially exploded bottom perspective view of the first embodiment.
Figure 6A:
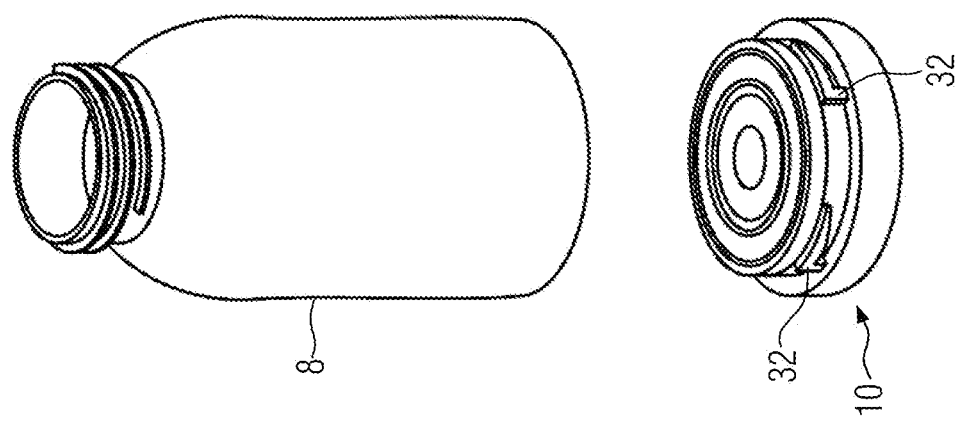
FIG. 6A shows a partially exploded top perspective view of the first embodiment.
Figure 8B:
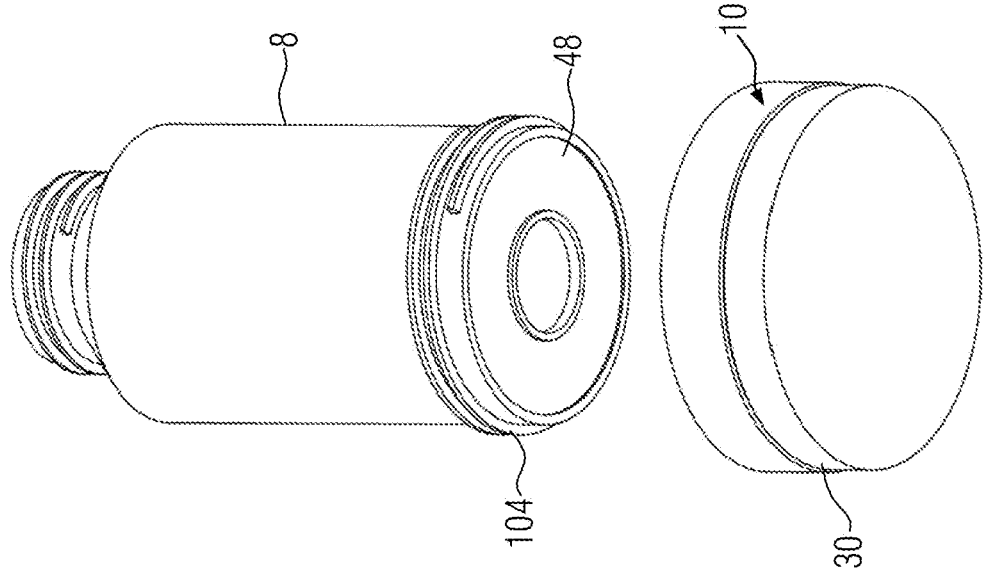
FIG. 8B shows a partially exploded bottom perspective view of the fourth embodiment.
Figure 8A:
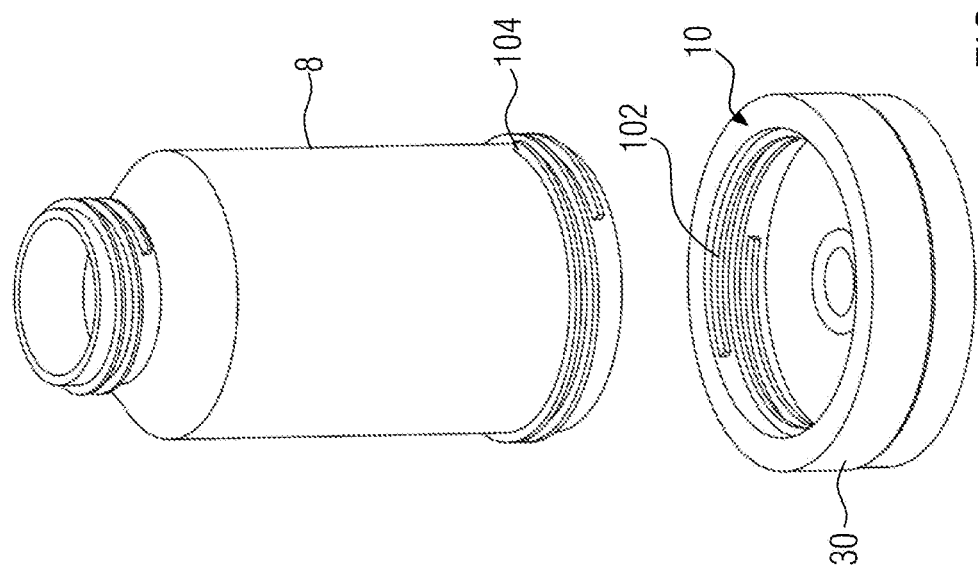
FIG. 8A shows a partially exploded top perspective view of a fourth embodiment.

FIGS. 5A and 5B show the sensor unit 34 of the first and the second embodiment which is arranged on a disk-shaped circuit board 72. FIG. 5A shows the upper side of the circuit board 72, on which a coil 74 is arranged. A hole 76 is provided at the center of the circuit board for air pressure equalization. Arranged at the outer edge region of the circuit board 72 are three through holes 78a, 78b, 78c, through each of which an attachment element can be passed. The outer edge of the circuit board 72 also has a notch 80 which allows for precise positioning during assembly.

FIG. 5B shows the underside of the circuit board 72 which is populated with batteries 82a, 82b, an on/off switch 84, a reset switch 86, a microprocessor 88 and a position sensor 90.

FIGS. 6 to 9 described hereafter relate to different embodiments, which, however, differ only in the connection mechanism for releasably connecting the bottle base 10 to the bottle body 8. The bottle body 8 there always comprises a ring-shaped flange 48 on the inner circumferential surface of the end section of the bottle body 8, facing the bottle base, against which the attachment section 58 of the membrane 28 sealingly abuts when the bottle base 10 is attached to the bottle body 8. FIGS. 6A, 6B relate to the first embodiment which comprises a bayonet lock. According to this embodiment, the housing 30 of the bottle base 10 forms locking arms 32. The locking arms 32 have an undercut 92 into which locking beads 94 of the bottle body can be introduced by a rotational motion once the bottle base has been inserted into the bottle body.

FIGS. 7A, 7B show a third embodiment with a screw connection. According to this embodiment, the housing 30 of the bottle base 10 forms an external thread 98 which interacts with an internal thread 100 formed on the bottle body 8. A fourth embodiment according to FIGS. 8A, 8B likewise has a screw connection, where the housing 30 of the bottle base 10 there forms an internal thread 102 which interacts with an external thread 104 formed on the bottle body 8.

FIGS. 9A, 9B show a fifth embodiment with a snap lock. According to this embodiment, the bottle base 10 comprises two oppositely disposed locking catches 106 which can be resiliently retained by manual operation of a touch pad 108, i.e. can be forced radially inwardly to move them behind a catch projection 110 formed on the bottle body 8 when the bottle base 10 is inserted into the bottle body 8 (only one locking catch can be seen in the figure). The catch projection 110 is there preferably formed as a circumferentially continuous bead on the inner circumferential surface of the end of the bottle body 8 facing the bottle base 10.

Figure 10:
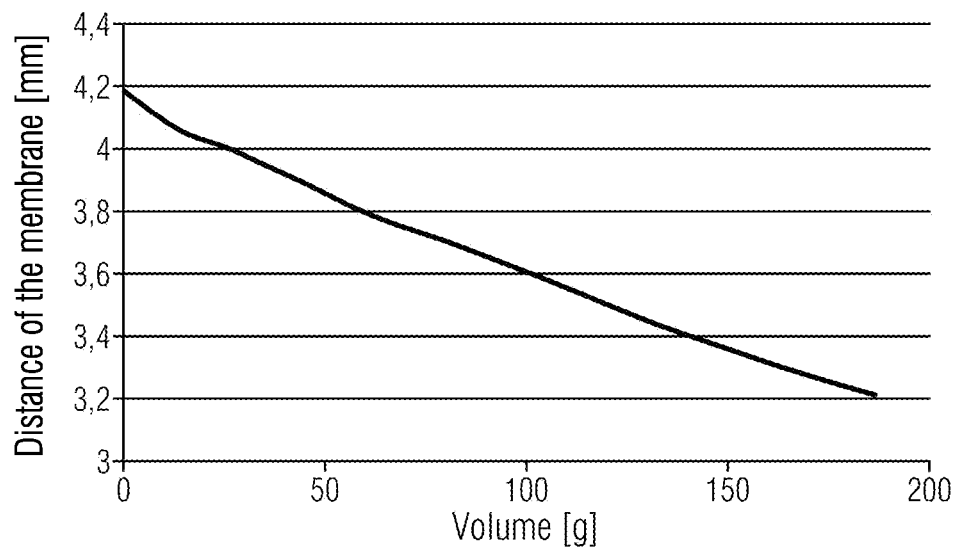
FIG. 10 shows a diagram illustrating the relationship between the distance of the membrane from the coil and the filling quantity of milk.

FIG. 10 shows a diagram which illustrates the relationship between the filling volume of milk in the baby bottle (expressed in grams) and the distance of the movable section 60 of the membrane 28 from the coil 74 of the sensor unit 34 (indicated in millimeters) for one embodiment. It arises from this diagram that this is a substantially linear relationship and that the distance decreases with an increasing filling quantity of milk. According to this embodiment, the membrane has a distance of 4.2 mm from the coil 74 when the baby bottle is empty.

Figure 11:
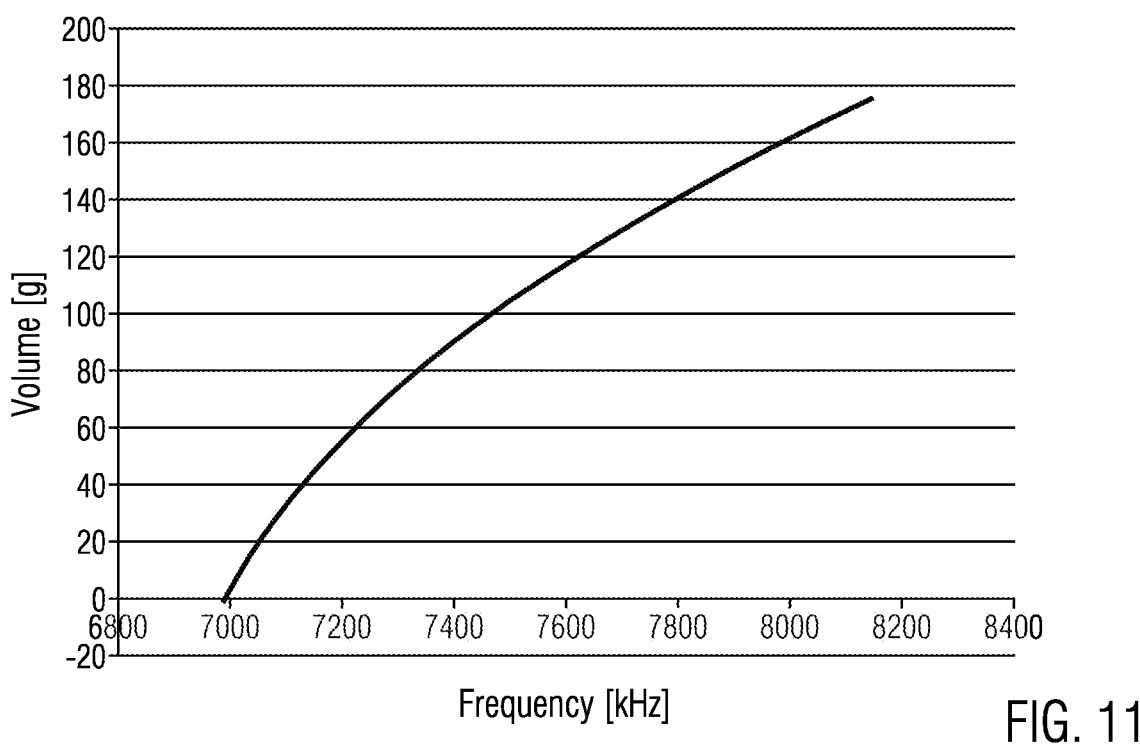
FIG. 11 shows a diagram illustrating the relationship between the filling quantity of milk and the output frequency of an RLC oscillator circuit.

FIG. 11 shows another diagram which illustrates the relationship between the filling volume of milk in the baby bottle (expressed in grams) and the output frequency of an RLC oscillator circuit (expressed in kilohertz) for one embodiment. This relationship is influenced by various parameters related to the geometry of the bottle, the frequency of the RLC oscillator circuit, and angle information due to signals from the position sensor 90 which typically detects the inclination of the bottle.

LIST OF REFERENCE NUMERALS 2 apparatus
4 connector
6 baby bottle
8 bottle body
10 bottle base
12 separating element
14 breast shield
16 connection for breast pump
18 funnel
20 bottleneck
22 fluid reservoir
24 external thread
26 bayonet lock
28 elastic membrane
30 housing
32 locking arm
34 sensor unit
36 housing cover
38 distance-bridging pin
40 mounting holes in the housing
42 mounting holes in the housing cover
44 bearing surface
46 housing flange
48 ring-shaped flange
50 upper side of the membrane
52 inner arcuated ring
54 center ring
56 outer ring
58 attachment section
60 movable section
62 edge flange
64 undercut
66 second flange
68 undercut
70 copper plate
72 circuit board
74 coil
76 hole
78 through holes
80 notch
82a battery
82b battery
84 on/off switch
86 reset switch
88 microprocessor
90 position sensor
92 undercut
94 locking bead
98 external thread
100 internal thread
102 internal thread
104 external thread
106 locking catch
108 touchpad
110 catch projection

What is claimed is:

1. An apparatus comprising:
    a connector;
    a baby bottle coupled thereto having a bottle body, a bottle base releasably attached to said bottle body, and a sensor unit arranged in said bottle base for determining a filling quantity of milk in said baby bottle
    and
    a sensor unit arranged in said bottle base for determining a filling quantity of milk in said baby bottle, wherein said sensor unit comprises a coil arranged centrally in said bottle base and spaced from a membrane in said baby bottle and having one of a centrally arranged metallic insert or a metallic coating, the membrane being impermeable to milk, elastic, and movable in the direction of said sensor unit.

2. The apparatus according to claim 1, wherein said membrane—when said baby bottle stands upright—moves toward said sensor unit when the filling quantity of milk increases and away from said sensor unit when the filling quantity of milk decreases.

3. The apparatus of claim 1, wherein the axis of said metallic insert is at least approximately aligned with the axis of said coil.

4. The apparatus according to claim 1, wherein electronic components are arranged between said coil and a bearing surface of said releasable bottle base formed by said bottle base.

5. The apparatus of claim 1, wherein said bottle base is attachable by one of screwing, a bayonet lock, or a snap lock, to said bottle body of said baby bottle.

6. A baby bottle with a bottle body, a bottle base releasably attached to said bottle body, and a sensor unit arranged in said bottle base for determining the amount of content in said baby bottle, wherein said sensor unit comprises a coil arranged centrally in said bottle base and spaced from a membrane having a centrally arranged metallic insert or a metallic coating, the membrane being impermeable to milk, elastic and movable in the direction of said sensor unit.

7. The baby bottle according to claim 6, wherein said membrane—when said baby bottle stands upright—moves toward said sensor unit when the filling quantity increases and away from said sensor unit when the filling quantity decreases.

8. The baby bottle according to claim 6, wherein the axis of said metallic insert is at least approximately aligned with the axis of said coil.

9. The baby bottle according to claim 6, wherein electronic components are arranged between said coil and a bearing surface of said releasable bottle base formed by said bottle base.

10. The baby bottle according to claim 6, wherein said bottle base is attachable by screwing, a bayonet lock, or a snap lock to said bottle body of said baby bottle.

\* \* \* \* \*